United States Patent [19]

Frank

[11] Patent Number: 5,321,173

[45] Date of Patent: Jun. 14, 1994

[54] INDANE COMPOUNDS AND COMPOSITIONS

[75] Inventor: Walter C. Frank, Holland, Pa.

[73] Assignee: Union Camp Corporation, Wayne, N.J.

[21] Appl. No.: 999,699

[22] Filed: Dec. 23, 1992

Related U.S. Application Data

[60] Division of Ser. No. 811,545, Dec. 20, 1991, Pat. No. 5,206,217, which is a continuation-in-part of Ser. No. 618,356, Nov. 21, 1990, Pat. No. 5,095,152.

[51] Int. Cl.$^5$ .................................. C07C 13/36
[52] U.S. Cl. .................................... 585/26
[58] Field of Search ........................ 585/26

[56] References Cited

U.S. PATENT DOCUMENTS

| | | |
|---|---|---|
| 3,278,622 | 10/1966 | Stofberg et al. ............. 568/327 |
| 3,509,215 | 4/1970 | Wood et al. ................. 568/327 |
| 3,992,432 | 11/1976 | Napier et al. ............... 260/604 |
| 4,018,719 | 4/1977 | Simone ....................... 512/6 |
| 4,143,065 | 3/1979 | Hoffmann et al. ............. 512/6 |
| 4,162,256 | 7/1979 | Sprecker et al. ............. 512/17 |
| 4,352,748 | 10/1982 | Traas et al. ................ 512/17 |
| 4,406,828 | 9/1983 | Gonzenbach et al. ........... 512/17 |
| 4,466,908 | 8/1984 | Sprecker et al. ............. 512/17 |
| 4,551,573 | 11/1985 | Cobb ......................... 585/449 |
| 4,568,782 | 2/1986 | Pagnotta et al. ............. 585/409 |
| 4,806,558 | 2/1989 | Wuest et al. ................ 514/385 |

FOREIGN PATENT DOCUMENTS

| | | |
|---|---|---|
| 0405427A2 | 6/1990 | European Pat. Off. . |
| 50-40761 | 4/1975 | Japan . |
| 1530433 | 2/1977 | United Kingdom . |

OTHER PUBLICATIONS

Bersuker et al., Chem. Abst., vol. 115, #89815h (1990).
Fehr et al., New Aromatic Musk Odorants: Design and Synthesis, (as reported in Helvetica Chimica Acta–vol. 72 1989), pp. 1537–1553.
French Patent No. 1,392,804 (as reported in Chemical Abstracts, vol. 63, p. 1681d (1965).
Kondo, et al., Sulfonium Salts as Liquid–Liquid Phase–Transfer Catalysts, (as reported in Communications, May 1988), pp. 403–404.
Organic Synthesis, Collective vol. 5, pp. 49–50 (John Wiley & Sons, 1973).
Carey, F. A. and Sundberg, R. J., Oxidation of Ketones and Aldehydes by Peroxidic Compounds and Oxygen, (as reported in Advanced Organic Chemistry), pp. 383–386 (1984).
British Patent No. 796,129 (as reported in Chemical Abstracts, vol. 53, pp. 6190–6191 (1958).
U.S. Pat. No. 2,851,501 (as reported in Chemical Abstracts, vol. 53, pp. 6190–6191 (1958).

Primary Examiner—James H. Reamer
Attorney, Agent, or Firm—Woodcock, Washburn, Kurtz, Mackiewicz & Norris

[57] ABSTRACT

The present invention relates to novel indane compounds, such as, for example, 5-formyl-1,1,2,3,3,4,6-heptamethylindane, a compound of the formula

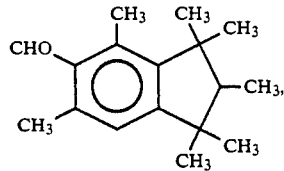

and to compositions including the same, as well as to methods for their preparation. Compounds and compositions of the invention possess a fragrant musk-like aroma and have utility in the perfumery and/or other industries.

8 Claims, No Drawings

INDANE COMPOUNDS AND COMPOSITIONS

RELATED APPLICATION

The is a division of application Ser. No. 811,545, filed Dec. 20, 1991, now U.S. Pat. No. 5,206,217, which is a continuation-in-part of Ser. No. 618,356, filed on Nov. 21, 1990, now U.S. Pat. No. 5,095,152, granted on Mar. 10, 1992.

BACKGROUND OF THE INVENTION

The present invention relates to novel acylated indane compounds and compositions having a fragrant musk-like aroma, and to processes for their preparation.

Musk fragrances are in great demand for use in various products such as in perfumes, colognes, cosmetics, soaps and others. However, natural musk, which is obtained from the Asian musk deer, is extremely scarce and is quite expensive. According, fragrance chemists have spent considerably time searching for synthetic products which duplicate or closely simulate this natural musk scent.

As a result of these research efforts, a number of different synthetic musks have been discovered. Among such synthetic compounds are the acetyl indanes described by U.S. Pat. No. 4,466,908, compounds of the formulas

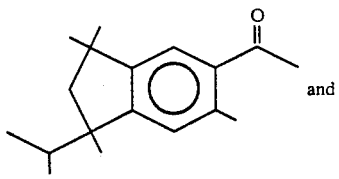

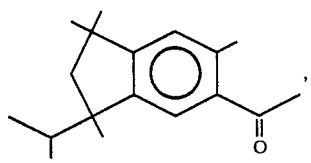

which may be employed, if desired, in combination with acetyl tetrahydronaphthalenes of the formula

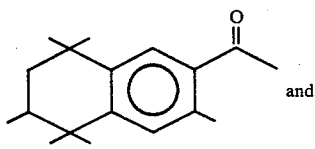

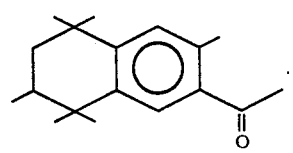

Similarly, Fehr et al., *Helvetica Chimica Acta.* Vol. 72, pp. 1537–1553 (1989) discusses such synthetic musks as those of the formula

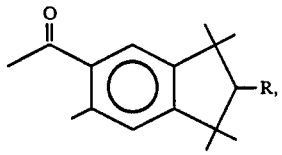

wherein R is either H or $CH_3$.

U.S. Pat. No. 4,352,748 discloses formylated and acetylated indane musks, including those of the formulas

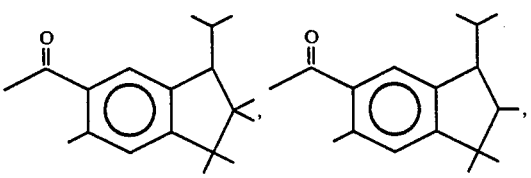

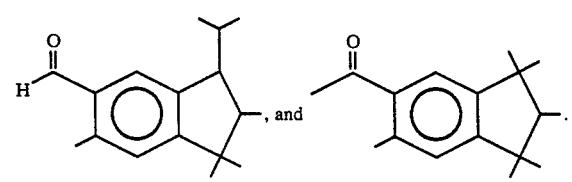

Other acetyl indanes, such as 6-acetyl-1,1,3,3,5-pentamethylindane, 5-acetyl-1,1,2,3,3-pentamethylindane and 6-acetyl-5-ethyl-1,1,2,3,3-pentamethylindane, are disclosed in French Pat. No. 1,392,804 (as reported in Chemical Abstracts, Vol. 63, p. 1681d (1965)).

Cobb et al., U.S. Pat. No. 4,551,573, also discusses certain indane compounds.

European Patent Publication 0 301 375 A2 describes formylated tetralins, such as 1,1,2,4,4-pentamethyl-6-formyl-1,2,3,4-tetrahydronaphthalene, and their utility as synthetic musks.

The foregoing references also describe methods for the preparation of indane compounds. For example, Cobb et al., U.S. Pat. No. 4,551,572 discloses a process for the alkylation of aromatic compounds with olefinic compounds in the presence of a catalyst consisting essentially of aluminum halide and elemental iodine. Examples of aromatic compounds described as suitable for use in the process include para-cymene, and olefinic compounds discussed include 2,3-dimethyl-2-butene, isobutylene and neohexene. A mixture of olefinic compounds can also be employed, in which case it is noted that one of the olefins may function as a sacrificial agent.

New and or better musk aroma compounds, as well as methods for their preparation, are needed. The present invention is directed to these, as well as other, important ends.

SUMMARY OF THE INVENTION

The present invention provides novel compounds of the formula [I]:

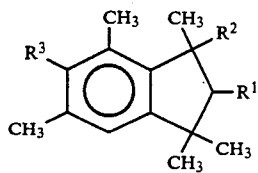

wherein
R[1] is H, CH$_3$, and CH$_2$CH$_3$,
R[2] is CH$_3$, and CH$_2$CH$_3$, and
R[3] is CHO, and OCHO, provided that
when R[1] and R[2] are both CH$_3$, R[3] is other than CHO.

The present invention also provides novel compositions comprising a compound which is 5-formyl-1,1,2,3,3,4,6-heptamethylindane, a compound of the formula [II]:

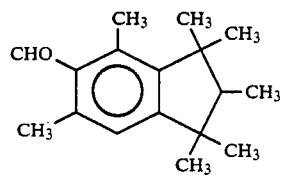

in combination with at least one compound selected from the group consisting of compounds of the formula [I]

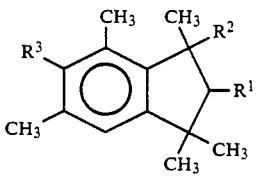

wherein
R[1] is H, CH$_3$, and CH$_2$CH$_3$,
R[2] is CH$_3$, and CH$_2$CH$_3$, and
R[3] is CHO, and OCHO,
provided that
when R[1] and R[2] are both CH$_3$, R[3] is other than CHO.

The foregoing compounds and compositions possess active musk aroma fragrances having utility in the perfumery and/or other industries. The compounds and compositions of the invention can be used alone or in combination with other compounds or ingredients.

Also provided are novel processes for the preparation of compounds of the formulas [I] and [II]. Such processes comprise contacting a compound selected from the group consisting of 5-isopropyl-meta-xylene and 5-isopropenyl-meta-xylene with a compound selected from the group consisting of 2-methyl-2-butene, 2-methylpropene, 2-methyl-1-butene, 3-methyl-2-pentene, 2-methyl-2-pentene and 3-methyl-3-hexene, or alternatively, contacting meta-xylene with 2,4-dichloro-2,3,4-trimethylpentane, each of the foregoing processes being carried out in the presence of a Lewis acid, a solvent, and optionally, a phase transfer agent, to form novel compounds of the formula [III];

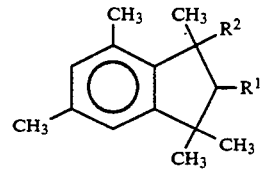

wherein
R[1] is H, CH$_3$, and CH$_2$CH$_3$, and
R[2] is CH$_3$ and CH$_2$CH$_3$.

These novel formula [III] compounds can then be formylated, or formylated and then oxidized, to form novel compounds of the formulas [I] and [II].

The present invention is further directed to the use of compounds of the formulas [I] and [II], with their highly active musk fragrance characteristics, as fragrance compositions.

DETAILED DESCRIPTION OF THE INVENTION

As noted above, the present invention is directed to novel musk compounds of the formula [I]:

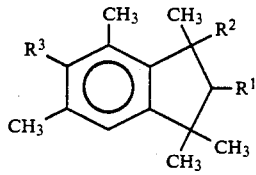

wherein
R[1] is H, CH$_3$, and CH$_2$CH$_3$,
R[2] is CH$_3$, and CH$_2$CH$_3$, and
R[3] is CHO, and OCHO,
provided that
when R[1] and R[2] are both CH$_3$, R[3] is other than CHO.
Preferably the formula [I] compounds are those compound wherein:
R[1] is CH$_3$, R[2] is CH$_2$CH$_3$, and R[3] is CHO, wherein R[1] and R[2] are located trans to one another (that is, on the opposite side of the indane ring plane), a compound which is trans-5-formyl-3-ethyl-1,1,2,3,4,6-hexamethylindane;
R[1] is H, R[2] is CH$_3$, and R[3] is OCHO, a compound which is 1,1,3,3,4,6-hexamethylindan-5-yl-formate;
R[1] is H, R[2] is CH$_3$, and R[3] is CHO, a compound which is 5-formyl-1,1,3,3,4,6-hexamethylindane;
R[1] is H, R[2] is CH$_2$CH$_3$, and R[3] is CHO, a compound which is 5-formyl-3-ethyl-1,1,3,4,6-pentamethylindane; and
R[1] is CH$_3$, R[2] is CH$_3$, and R[3] is OCHO, a compound which is 1,1,2,3,3,4,6-heptamethylindan-5-yl-formate.
The present invention is also directed to a novel musk compound of the formula [II]:

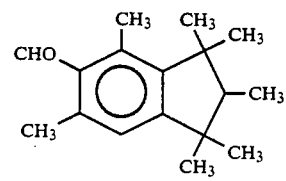

a compound which is 5-formyl-1,1,2,3,3,4,6-heptamethylindane.

The formula [I] and [II] compounds or compositions may be employed alone, or in combination with one another, as compositions useful in the perfumery or other industries. A particularly preferred composition is one comprising, in combination, formula [I] compounds which are cis-5-formyl-3-ethyl-1,1,2,3,4,6-hexamethylindane, trans-5-formyl-3-ethyl-1,1,2,3,4,6-hexamethylindane, 1,1,3,3,4,6-hexamethylindan-5-yl-formate, 5-formyl-1,1,3,3,4,6-hexamethylindane, 5-formyl-3-ethyl-1,1,3,4,6-pentamethylindane, and 1,1,2,3,3,4,6-heptamethylindan-5-yl-formate, and the formula [II] compound 5-formyl-1,1,2,3,3,4,6-heptamethylindane.

The novel indane compounds and compositions of the invention can be prepared in various fashions. In the preferable protocol, compounds of the formula [III] are first prepared, and are then formylated, or formylated and oxidized, to yield the compounds of formulas [I] and [II].

Preferably the compounds of formula [III] are prepared by contacting a compound selected from the group consisting of 5-isopropyl-meta-xylene and 5-isopropenyl-meta-xylene with a compound selected from the group consisting of 2-methyl-2-butene, 2-methyl-propene (also referred to as isobutylene), 2-methyl-1-butene, 3-methyl-2-pentane, 2-methyl-2-pentane and 3-methyl-3-hexene, In another preferable process, the compound of formula [III] wherein $R^1$ and $R^2$ are both $CH_3$ is prepared by contacting meta-xylene with 2,4-dichloro-2,3,4-trimethylpentane. The foregoing reactants can be synthesized using conventional organic synthesis procedures and/or purchased from various commercial sources. For example, a product containing 98% 2-methyl-2-butene is sold by Aldrich Chemical Company, Milwaukee, Wisconsin, under the trademark Isoamylene ™. In carrying out the foregoing processes, the reactants are combined with a Lewis acid or a protonic acid, a solvent which can be a halogenated or unhalogenated solvent, and optionally, a phase transfer agent, to form the compounds of formula [III]. As those skilled in the art would recognize, a Lewis acid can be employed with any of the reactants, while the protonic acid is employed only in connection with those reactions involving the reactant 5-isopropenyl-meta-xylene.

Any of the Lewis acids, that is, any non-protonic compounds capable of accepting an electron pair, are suitable for use in the foregoing process. Exemplary Lewis acids include metal halides such as aluminum halides, including aluminum chloride, aluminum bromide, aluminum iodide, monofluorodichloroaluminum, monobromodi-chloroaluminum and monoiododichloroaluminum. Alkyl metals and alkyl metal halides suitable for use as Lewis acids in the present process are disclosed, for example, in Kennedy, Joseph P., *Carbocationic Polymerization*, p. 221 (Wiley-Interscience Publishers, 1982), the disclosures of which are incorporated herein by reference. In the subject process, aluminum halides are preferred. Of the aluminum halides, aluminum chloride and aluminum bromide, particularly aluminum chloride ($AlCl_3$), are most preferred.

Any of the protonic acids are suitable for use with the foregoing processes involving the reactant 5-isopropenyl-meta-xylene. Exemplary protonic acids include sulfuric acid, phosphoric acid, methane sulfonic acid, para-toluene sulfonic acid, and the like.

Halogenated solvents suitable for use in the process are varied, and include halogenated aliphatic, halogenated alicyclic and halogenated aromatic hydrocarbon solvents. Particularly preferred are the halogenated aliphatic hydrocarbons. Suitable halogenated solvents include, for example, 1,2-dichloroethane, 1,1-dichloroethane, trichloromethane, dichloromethane, 1,1,2,2-tetrachloroethylene, 1,2-dichloroethylene, 1,2,3-trichloropropane, 1,1,2-trichloroethane, monochlorobenzene, fluorobenzene, and orthodiohlorobenzene. Particularly preferred halogenated solvents include dichloromethane, trichloromethane and 1,2-dichloroethane.

As an alternative to or in combination with halogenated solvents, one may employ unhalogenated solvents. A variety of unhalogenated solvents may be utilized, including, unhalogenated aliphatic, unhalogenated alicyclic and unhalogenated aromatic hydrocarbon solvents. Such unhalogenated solvents are generally preferred over the halogenated solvents for reasons of safety. Particularly preferred are the unhalogenated aliphatic and unhalogenated alicyclic hydrocarbons. Suitable unhalogenated solvents include, for example, the aliphatic hydrocarbon solvents n-hexane, n-heptane and n-octane, the alicyclic hydrocarbon solvent cyclohexane, and the aromatic hydrocarbon solvents benzene and mesitylene (1,3,5-trimethyl-benzene). A particularly preferred unhalogenated solvent is the unhalogenated alicyclic hydrocarbon solvent cyclohexane.

Phase transfer agents suitable for use in the process include onium salts such as ammonium, phosphonium and sulfonium salts. Other phase transfer agents suitable for use in the present process will be readily apparent to those skilled in the art, once having been made aware of the present disclosure.

Examples of ammonium phase transfer agents include quaternary ammonium halides such as methyltrioctylammonium chloride, methyltrinonylammonium chloride, methyltridecylammonium chloride, hexadecyltrihexylammonium bromide, ethyltrioctylammonium bromide, didodecyldimethylammonium chloride, tetraheptylammonium iodide, dioctadecyldimethylammonium chloride, tridecylbenzylammonium chloride, ditricosylmethylammonium chloride, and homologues thereof having chlorine, fluorine, bromine or iodine atoms substituted for the enumerated halide atom.

Exemplary phosphonium phase transfer agents include quaternary phosphonium halides such as tributyldecylphosphonium iodide, triphenyldecylphosphonium iodide, tributylhexadecylphosphonium iodide, and homologues thereof having chlorine, fluorine or bromine atoms substituted for the iodine atom.

Representative sulfonium phase transfer agents include ternary sulfonium halides such as lauryldimethylsulfonium iodide, lauryldiethylsulfonium iodide and tri(n-butyl)sulfonium iodide, and homologues thereof having chlorine, fluorine or bromine atoms substituted for the iodine atom.

These and other suitable phase transfer agents are described, for example, in Napier et al., U.S. Pat. No. 3,992,432 entitled "Phase Transfer Catalysis of Heterogenous Reactions by Quaternary Salts", and in Kondo et al., *Synthesis*, pp. 403–404 (May 1988), the disclosures of which are incorporated herein by reference.

Preferable phase transfer agents are ammonium or sulfonium salts, particularly quaternary ammonium or ternary sulfonium halides. Most preferred are quaternary ammonium halides, particularly methyltrioctylammonium chloride, and a mixture of methyltrioctylammonium chloride and methyltridecylammonium chloride. The latter mixture is marketed under the trademark Adogen-464 TM, by Sherex Co., located in Dublin, Ohio.

In general, the molar proportions of the reagents employed in the process can be varied over a relatively wide range, the particular amount to be employed being well within the ambit of those skilled in the art, once armed with the present disclosures. For best results, however, it is important to maintain a ratio of less than one mole of phase transfer agent per mole of Lewis acid. Preferably, the molar ratio is about 0.8 to 1.0, more preferably about 0.5 to 1.0, phase transfer agent to Lewis acid. It should be noted that some phase transfer agents sold commercially are sold in an impure form. Such impurities usually comprise water or an alcohol species. Water and alcohol, as well as other impurities, will react adversely with the Lewis acid, thereby lowering the amount of Lewis acid available for the process of the present invention. Accordingly, where the phase transfer agent added contains such impurities, the amount of Lewis acid should be increased to account for these impurities. In such a situation, the ratio of transfer agent to Lewis acid might be about 0.3 to 1.0. Such impure agent-containing mixtures are referred to herein as mixtures in an "impure form".

The process can be carried out in any suitable vessel which provides sufficient contacting between the Lewis acid, the phase transfer agent and the reactants. For simplicity, a stirred batch reactor can be employed. Although stirring is recommended to provide efficient contact between reactants, it has been found that in the halogenated solvent, or in the unhalogenated solvent plus phase transfer agent and/or solvent, the Lewis acid is able to solubilize rather quickly, thereby obviating the need for stringent stirring requirements. The reaction vessel used should be resistant to the possible corrosive nature of the Lewis acid. Glass-lined vessels are suitable for this purpose, as well as other vessel materials well-known in the art.

The reagents may be added to the vessel in any order, although generally the solvent, any phase transfer agent, and Lewis acids or protonic acids are added first, followed by reactant addition.

Ideally, the reaction is carried out at temperatures ranging from about −30° C. to about 50° C., preferably temperatures ranging from about −10° C. to about 30° C., and most preferably at temperatures ranging from about 0° C. to about 20° C.

The pressure at which the reaction is carried out is not critical. If the reaction is carried out in a sealed vessel, autogenous pressure is acceptable, although higher or lower pressures, if desired, may be employed. The reaction may also be carried out at atmospheric pressure in an open reaction vessel, in which case, the vessel is preferably equipped with a moisture trap to prevent significant exposure of Lewis acid to moisture. The reaction may take place in an oxygen atmosphere or an inert atmosphere, as in the presence of a gas such as nitrogen, argon and the like, the type of atmosphere also not being critical.

Reaction time is generally rather short and is often dictated by the type of equipment employed. Sufficient time should be provided, however, for thorough contacting of the reactants, the Lewis acid, the solvent, and any phase transfer employed. Generally, the reaction proceeds to equilibrium in about 1 to about 8 hours.

Preferably, the foregoing processes are carried out in the substantial absence of elemental iodine ($I_2$). By "substantial absence", it is meant that only a deminimus amount of iodine (such as, for example, less than 1% by weight of $I_2$ based on the weight of the Lewis acid, if any, is present in the reaction medium. Preferably, the reaction medium is devoid of any elemental iodine.

As those skilled in the art will recognize once armed with the present disclosure, by selecting from among the different reactants, different formula [III] compounds may be preferentially prepared, as illustrated in Table I below.

TABLE I

| Reactant 1 | Reactant 2 | Preferential Product |
|---|---|---|
| 5-isopropyl-meta-xylene and/or 5-isopropenyl-meta-xylene | 2-methyl-2-butene | Formula [III] wherein $R^1 = CH_3$ and $R^2 = CH_3$ |
| 5-isopropyl-meta-xylene and/or 5-isopropenyl-meta-xylene | 2-methylpropene (isobutylene) | Formula [III] wherein $R^1 = H$ and $R^2 = CH_3$ |
| 5-isopropyl-meta-xylene and/or 5-isopropenyl-meta-xylene | 2-methyl-1-butene | Formula [III] wherein $R^1 = H$ and $R^2 = CH_2CH_3$ |
| 5-isopropyl-meta-xylene and/or 5-isopropenyl-meta-xylene | 2-methyl-2-pentene | Formula [III] wherein $R^1 = CH_3$ and $R^2 = CH_2CH_3$ |
| 5-isopropyl-meta-xylene and/or 5-isopropenyl-meta-xylene | 2-methyl-2-pentene | Formula [III] wherein $R^1 = CH_2CH_3$ and $R^2 = CH_3$ |
| 5-isopropyl-meta-xylene and/or 5-isopropenyl-meta-xylene | 3-methyl-3-hexene | Formula [III] wherein $R^1 = CH_2CH_3$ and $R^2 = CH_2CH_3$ |
| meta-xylene | 2,4-dichloro-2,3,4-trimethylpentane | Formula [III] wherein $R^1 = CH_3$ and $R^2 = CH_3$ |

Product can be recovered from the reaction mixture by first quenching the reaction mixture in cold water or on crushed ice, preferably on ice, and then processing the mixture in the usual manner for Friedel-Crafts reactions to extract the desired compounds of Formula [III]. Typically, following quenching and the resultant phase separation, the organic layer is washed an additional time with water to aid in removal of the Lewis acid. One or more additional washings can be carried out with dilute alkali solution to further aid Lewis acid removal. Still further purification may be carried out, for example, using standard fractional distillation techniques, as well as other conventional extraction, distillation, crystallization and chromatography techniques, and the like. Suitable extraction and separation protocol is described, for example, in George A. Olah, *Friedel-Crafts And Related Reactions*, Vols. 1 and 2 (Interscience Publishers, John Wiley and Sons, 1964), the disclosures of which are hereby incorporated herein by reference, in its entirety.

Preferably the formula [III] compounds are those compounds wherein:

$R^1$ is $CH_3$, and $R^2$ is $CH_2CH_3$, wherein $R^1$ and $R^2$ are located cis to one another (that is, on the same side of the indane ring plane), a compound which is cis-3-ethyl-1,1,2,3,4,6-hexamethylindane;

$R^1$ is $CH_3$, and $R^2$ is $CH_2CH_3$, wherein $R^1$ and $R^2$ are located trans to one another (that is, on the opposite side of the indane ring plane), a compound which is trans-3-ethyl-1,1,2,3,4,6-hexamethylindane;

$R^1$ is H, and $R^2$ is $CH_3$, a compound which is 1,1,3,3,4,6-hexamethylindane;

$R^1$ is H, and $R^2$ is $CH_2CH_3$, a compound which is 3-ethyl-1,1,3,4,6-pentamethylindane; and $R^1$ is $CH_3$, and $R^2$ is $CH_3$, a compound which is 1,1,2,3,3,4,6-heptamethylindane.

The formula [III] compounds may be employed alone, or in combination with one another, as compounds or compositions useful as reagents in the preparation of the formula [I] and [II] compounds. A particularly preferred composition is one comprising, in combination, the formula [III] compounds which are cis-3-ethyl-1,1,2,3,4,6-hexamethylindane, trans-3-ethyl-1,1,2,3,4,6-hexamethylindane, 1,1,3,3,4,6-hexamethylindane, 3-ethyl-1,1,3,4,6-pentamethylindane, and 1,1,2,3,3,4,6-heptamethylindane.

The novel indane compounds of formula [III] can be formylated, that is, converted to compounds of formula [I] wherein $R^3$ is CHO (carboxaldehydes), using conventional formylation technology, producing compounds having a very fine, musk-like fragrance, a characteristic which renders them highly valuable for use in the perfumery industry.

Specifically, to produce the formylated compounds of the invention, the unformylated compounds of formula [III] are preferably reacted with α,α-dichloromethyl methyl ether, in a solvent such as an organic solvent, preferably a halogenated organic solvent such as, for example, anhydrous methylene chloride, in the presence of a Lewis acid. Other suitable halogenated solvents are as discussed above in connection with the preparation of the formula [III] compounds. Such formylation methods are well known in the art and are described, for example, in *Organic Synthesis*, Collective Vol. 5, pp. 49–50 (John Wiley & Sons, 1973), the disclosures of which are incorporated herein by reference, in their entirety.

If desired, the compounds of formula [I] wherein $R^3$ is CHO, may then be oxidized, that is, converted to compounds of formula [I] wherein $R^3$ is OCHO (formate esters), using conventional oxidation technology, producing further compounds having a very fine, musk-like fragrance, a characteristic which renders them highly valuable in the perfumery industry.

Specifically, to produce the formate ester compounds of the invention, a Bayer-Villager-type reaction is preferably employed. In accordance with that process, the formylated compounds may be reacted with a peracid, preferably meta-chloro-perbenzoic acid, in a solvent such as an organic solvent, preferably a halogenated organic solvent such as, for example, anhydrous methylene chloride. Other suitable halogenated solvents are as discussed above in connection with the preparation of the formula [III] compounds. Such oxidation methods are discussed, for example, in Carey, Francis A., and Richard J. Sundberg, *Advanced Organic Chemistry*, Part B, pp. 383–386 (Plenum Press, New York 1977), the disclosures of which are incorporated herein by reference, in their entirety.

Further purification of the formylated, or formylated and oxidized, compounds of formulas [I] and [II] may be carried out, if desired, using, for example, standard fractional distillation techniques, as well as other conventional extraction, distillation, crystallization and chromotography techniques, and the like.

The compounds of formulas [I] and [II] of the invention have high utility in the fragrance industry. These compounds can be used alone or in combination with one another or with one or more ingredients to provide a musky fragrance composition.

For example, the formula [I] and [II] compounds of the invention may be used as olfactory components in anionic, cationic, nonionic and zwitterionic detergents, soaps, fabric softener compositions, fabric softener articles for use in clothes dryers, space odorants and deodorants, perfumes, colognes, toilet water, toiletries, bath preparations, deodorants, cosmetics, hand lotions, sunscreens, powders, as well as in other ways. The amount of the indane to be used in augmenting or enhancing the aroma of such compositions will vary depending upon the particular use intended, as will be readily apparent to those skilled in the art. Although they may be present in major or minor amounts, preferably, because of the strength of their odor, the compounds of the invention are generally employed as a minor ingredient, that is, in an amount of about 0.01% by weight of the fragrance composition up to about 50% by weight of the fragrance composition, preferably about 0.05% by weight up to about 30% by weight of the fragrance composition, and most preferably about 0.1% by weight up to about 5.0% by weight of the fragrance composition.

The fragrance composition of the invention may, if desired, contain a vehicle or carrier (as used herein the term "carrier" shall be considered synonymous with the term "vehicle"). Such carriers include liquids such as a non-toxic alcohol, a non-toxic glycol, or the like. An example of a non-toxic alcohol is ethyl alcohol. An example of a non-toxic glycol is 1,2-propylene glycol. Alternatively, the carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular use intended, as will be readily apparent to those skilled in the art. However, the vehicle or carrier can generally be employed in an amount of about 5% by weight up to about 95% by weight of the fragrance composition.

The fragrance composition may, if desired, contain other perfumery materials. Typical additional perfumery materials which may form part of compositions of the invention include: natural essential oils such as lemon oil, mandarin oil, clove leaf oil, petitgrain oil, cedar wood oil, patchouli oil, lavandin oil, neroli oil, ylang oil, rose absolute or jasmine absolute; natural resins such as labdanum resin or olibanum resin; single perfumery chemicals which may be isolated from natural sources or manufactures synthetically, as for example, alcohols such as geraniol, nerol, citronellol, linalol, tetrahydrogeraniol, beta-phenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate; and other materials commonly employed in the art of perfumery. Typically at least five, and usually at least ten, of such materials will be present as components of the active ingredient. The amount of the additional perfumery material will vary depending upon the particular perfumery material employed and use intended, as will be apparent to those skilled in the art.

Fragrance compositions and preparatory techniques are well known in the art, and are disclosed, for example, in "Soap, Perfumery and Cosmetics", by W.A. Poucher, 7th edition, published by Chapman & Hall (London) (1959); "Perfume and Flavour Chemicals", by S. Arctander, published by the author (Montclair) (1959); and "Perfume and Flavour Materials of Natural Origin", also by S. Arctander, self-published (Elizabeth, NJ) (1960), the disclosures of each of which are incorporated herein by reference, in their entirety.

The present invention is further described in the following Examples. These Examples are not to be construed as limiting the scope of the appended claims.

In each Example, results were analyzed on both polar and non-polar gas chromatography columns. All gas chromatography analyses were carried on capillary columns using a weight percent internal standard method of analysis. Structural identifications were assigned based on a combination of GCMS fragmentation patterns and the spectroscopic techniques of NMR and IR compared to standards.

Example 1 describes the preparation of 1,1,2,3,3,4,6-heptamethylindane and other indane compounds. Example 2 discusses the synthesis of 5-formyl-1,1,2,3,3,4,6-heptamethylindane and other carboxaldehyde and formate ester indane compounds using the compounds of Example 1. Example 3 reports the testing of the indane compounds of Example 2 for fragrance properties.

EXAMPLES

EXAMPLE 1

A 100 ml four-necked round bottom flask equipped with an $N_2$ line, condenser, thermocouple-temperature controller, and addition funnel was charged with $CH_2Cl_2$ (9.79 g), and cooled to 15°p0 C. with a dry ice/isopropanol bath. To the flask was then added, with stirring, anhydrous $AlCl_3$ (0.874 g). While maintaining a temperature of 15° C., a homogeneous mixture of 5-isopropy-meta-xylene (21.7 g, 0.1466 moles) and 2-methyl-2-butene (20.53 g, 0.2932 moles) was added to the flask over a period of about 30 minutes. The reaction was then allowed to proceed for about 2 additional hours at the same temperature. The flask contents were continuously stirred throughout the reaction.

The reaction was then quenched with cold deionized water (10 ml), and the resultant product further treated with 10% aqueous $NaHCO_3$ and extracted with $CH_2Cl_2$. After drying with anhydrous $Na_2SO_4$, the organic solution was rotoevaporated to give about 30 g of crude product containing about 50 weight percent of 1,1,2,3,3,4,6-heptamethylindane, in addition to other indane compounds.

EXAMPLE 2

To a 1l three-necked flask equipped with a reflux condenser, a stirrer, and a dropping funnel, was charged 21.6 g of the crude product containing about 50 weight percent 1,1,2,3,3,4,6-heptamethylindane from Example 1, and 115 ml anhydrous $CH_2Cl_2$. The solution was then cooled in an ice bath, and 31.61 g (18.3 ml, 0.166 moles) $TiCl_4$ was added over a period of about 3 minutes. While the solution is stirred and cooled, 9.53 g (7.5 ml, 0.083 moles) $\alpha,\alpha$-dichloromethyl methyl ether was added dropwise over a 10 minute period, while maintaining a temperature of about 0° to about 5° C. After the addition is complete, the mixture is stirred for about 20 minutes in an ice bath, for about 30 minutes without cooling, and finally for about 15 minutes at 35° C.

The reaction mixture was then poured into a separatory funnel containing about 0.2 kg of crushed ice and shaken thoroughly. The organic layer is separated, and the aqueous solution is extracted with two 50 ml portions of methylene chloride. The combined organic solution is washed three times with 50 ml portions of water. A crystal of hydroquinone is added to the methylene chloride solution which is then dried over anhydrous sodium sulfate. After evaporation of the solvent, the residue is distilled to give 21.82 g of crude product containing 53.5% of 5-formyl-1,1,2,3,3,4,6-heptamethylindane, or further distilled using conventional techniques to yield a more purified indane product containing 77.0% of 5-formyl-1,1,2,3,3,4,6-heptamethylindane, 3.2% of cis-5-formyl-3-ethyl-1,1,2,3,4,6-hexamethylindane, 5.5% of trans-5-formyl-3-ethyl-1,1,2,3,4,6-hexamethylindane, 0.05% 1,1,3,3,4,6-hexamethylindan-5-yl-formate, 1.2% of 5-formyl-1,1,3,3,4,6-hexamethylindane, 4.8% of 5-formyl-3-ethyl-1,1,3,4,6-pentamethylindane, and 0.7% of 1,1,2,3,3,4,6-heptamethylindan-5-yl-formate.

EXAMPLE 3

The more purified indane product of Example 2 was distilled using standard fractional distillation techniques. Each indane was then tested for its fragrance characteristics by qualified fragrance testers. The results are shown in Table II below.

TABLE II

| Indane Compound Tested | Fragrance Characteristics |
|---|---|
| 5-formyl-1,1,2,3,3,4,6-heptamethylindane | sweet musk character |
| cis-5-formyl-3-ethyl-1,1,2,3,4,6-hexamethylindane | some sweet musk character, with a slight burnt caramel note |
| trans-5-formyl-3-ethyl-1,1,2,3,4,6-hexamethylindane | sweet musk with a slightly fatty note |
| 1,1,3,3,4,6-hexamethylindan-5-yl-formate | some musk character with a green floral note |
| 5-formyl-1,1,3,3,4,6-hexamethylindane | powdery musk character, slightly sweet |
| 5-formyl-3-ethyl-1,1,3,4,6-pentamethylindane | strong, fruity, powdery, sweet musk character |
| 1,1,2,3,3,4,6-heptamethylindan-5-yl-formate | some musk character |

What is claimed is:

1. A compound of the formula [III]

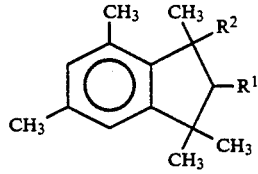

wherein
R$^1$ is H, CH$_3$, and CH$_2$CH$_3$, and
R$^2$ is CH$_3$ and CH$_2$CH$_3$.

2. A compound of claim 1 which is cis-3-ethyl-1,1,2,3,4,6-hexamethylindane.

3. A compound of claim 1 which is trans-3-ethyl-1,1,2,3,4,6-hexamethylindane.

4. A compound of claim 1 which is 1,1,3,3,4,6-hexamethylindane.

5. A compound of claim 1 which is 3-ethyl-1,1,3,4,6-pentamethylindane.

6. A compound of claim 1 which is 1,1,2,3,3,4,6-heptamethylindane.

7. A composition comprising at least two compounds of the formula [III]

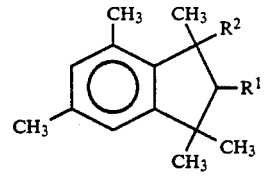

wherein
R$^1$ is H, CH$_3$, and CH$_2$CH$_3$, and
R$^2$ is CH$_3$ and CH$_2$CH$_3$.

8. A composition of claim 7 wherein the formula [III] compounds comprise, in combination, compounds which are cis-3-ethyl-1,1,2,3,4,6-hexamethylindane, trans-3-ethyl-1,1,2,3,4,6-hexamethylindane, 1,1,3,3,4,6-hexamethylindane, 3-ethyl-1,1,3,4,6-pentamethylindane, and 1,1,2,3,3,4,6-heptamethylindane.

* * * * *